United States Patent
Mateu et al.

(10) Patent No.: US 7,211,245 B2
(45) Date of Patent: May 1, 2007

(54) STRETCH-MASCARA

(75) Inventors: Juan Mateu, Milton, NJ (US); Ralph Macchio, Sparta, NJ (US); Rupali Kulkarni, Bridgewater, NJ (US); Domnica Cernasov, Ringwood, NJ (US)

(73) Assignee: Coty B.V. (NL)

( * ) Notice: Subject to any disclaimer, the term of this patent is extended or adjusted under 35 U.S.C. 154(b) by 711 days.

(21) Appl. No.: 10/398,962

(22) PCT Filed: Oct. 5, 2001

(86) PCT No.: PCT/EP01/11504

§ 371 (c)(1),
(2), (4) Date: Apr. 11, 2003

(87) PCT Pub. No.: WO02/30368

PCT Pub. Date: Apr. 18, 2002

(65) Prior Publication Data

US 2004/0013624 A1  Jan. 22, 2004

(30) Foreign Application Priority Data

Oct. 13, 2000  (DE) ............................... 100 53 052

(51) Int. Cl.
*A61Q 1/10* (2006.01)
(52) U.S. Cl. ............... 424/70.7; 424/70.11; 424/70.12; 424/70.15
(58) Field of Classification Search ............... None
See application file for complete search history.

(56) References Cited

U.S. PATENT DOCUMENTS

| 5,154,916 | A | 10/1992 | Arraudeau et al. |
| 5,389,363 | A | 2/1995 | Snyder et al. |
| 5,874,072 | A | 2/1999 | Alwattari et al. |
| 5,876,704 | A | 3/1999 | Collin et al. |
| 6,482,400 | B1 * | 11/2002 | Collin .................. 424/70.6 |
| 6,491,931 | B1 * | 12/2002 | Collin .................. 424/401 |
| 6,503,521 | B1 * | 1/2003 | Atis et al. ............... 424/401 |
| 6,534,047 | B1 * | 3/2003 | Bodelin ............... 424/70.7 |
| 6,607,734 | B1 * | 8/2003 | Afriat .................... 424/401 |

FOREIGN PATENT DOCUMENTS

WO   WO 00/74159 A2   12/2000

* cited by examiner

*Primary Examiner*—Jyothsna Venkat
(74) *Attorney, Agent, or Firm*—Akerman Senterfitt

(57) ABSTRACT

The invention relates to a novel cosmetic product with special flexibility and stretching characteristics, so-called "stretch-mascara". The mascara has an oil phase and an aqueous phase, said oil phase containing 2 to 10 wt. % of an unbranched polyethylene wax with a molecular weight of 400 to 1500 Dalton, in relation to the weight of the oil phase, and at least one other wax or oil or mixture thereof. The aqueous phase contains 0.5 to 5% of a film former PVP/PVP-VA, polyquaternium-46 and mixtures thereof. The product also contains 0.5 to 20 wt. % of an external film former phase with a water-soluble film former selected from the group PEG/PPG-25/25 dimethicone/carylates/t-butyl acrylates copolymer, polyurethane-1 and mixtures thereof.

10 Claims, No Drawings

STRETCH-MASCARA

CROSS REFERENCE TO RELATED APPLICATION

This application is a national stage of PCT/EP01/11504 filed Oct. 5, 2001 and based upon DE 100 53 052.4 filed October 13, 2000 under the International Convention.

BACKGROUND OF THE INVENTION

1. Field of the Invention

The present invention relates to a novel cosmetic product called "stretch mascara" having special stretching features.

2. Description of the Related Art

WO99/22711 discloses a waterproof mascara compound based on a styrene ethylene propylene copolymer basis acting as a jelling agent and in which, among others, polyethylene wax can be used as film-forming agent. It is possible to obtain mascara compounds having the usual viscosity values of approximately 1,500,000 Pa·s (cP).

SUMMARY OF THE INVENTION

It is an object of the present invention to provide mascara compounds having lower viscosity values and an excellent extensibility to be used as mascara to be applied to the eyelashes.

DETAILED DESCRIPTION OF THE INVENTION

According to the present invention, the novel stretch mascara based on an oil phase and an aqueous phase, wherein a) the oil phase comprises 2 to 10% by weight, related to the weight of the oil phase, an unbranched polyethylene having a molecular weight distribution ranging between 400 and 1,500 Dalton, and at least one further oil or wax or mixture thereof;

b) the water phase comprises 0.5 to 5% by weight of a film-forming agent for the water phase selected from the group consisting of PVP/PVP-VA, Vinylcaprolactam/Vinylpyrrolidon/quaternized Vinylimidazol (Polyquaternium-46) and mixtures thereof, where the % by weights are related to the total weight of the mascara;

c) additionally 0.5 to 20% by weight of an external phase of a film-forming agent comprising a water soluble film-forming agent selected from the group consisting of PEG/PPG-25/25 Dimethicone/-Acrylates/t-Butyl Acrylates Copolymer, Polyurethane-1 and mixtures thereof, where the % by weights are related to the total weight of the mascara; and d) further cosmetic pigments, carriers and auxiliary substances by 100% by weight.

The oil phase may further comprise natural waxes, other synthetic waxes, emollients, higher $C_{12}$–$C_{20}$ fatty acid esters, emulsifying agents, protective agents and mixtures thereof. The share of the oil phase ranges between 10 and 40 weight percent, related to the weight of the mascara.

In the oil phase the unbranched polyethylene is contained with a molecular distribution of 400 to 1,500 Dalton, preferably with a molecular weight of 400 to 600 Dalton to receive a special flexible product by that. The polyethylene has a melting point of 75–99° C. and a penetration value of 5–15 dyn/mm at 25° C.

The measurement of the penetration value takes place with a penetrometer, eg. Lab-Line #4101, manufactured by Lab-Line Instruments Inc., USA, needle D1321. A sample is heated to its pouring temperature, poured in a eight-ounce jar filled to the shoulder of the jar and covered, and allowed to cool for 12–24 hours in a controlled environment at 20° C. After that the cover is peeled off from the jar and measurements be taken.

The needle is mounted in the penetrometer head, a required weight, if needed, is added to the loading bar and the measuring head is lowered so that the tip of the needle touches the surface of the sample. After that the plunger is released gently and the cone let be penetrated the sample for 5 sec. Then the measured value is read. Four values are taken from different places of the sample and reported as an average.

The penetration value ranging between 5 and 15 dyn/mm at 25° C. reflects the flexibility and softness of this wax.

The other waxes are preferably selected among candelilla wax, beeswax, stearic acid, glyceryl monostearate and mixtures thereof. The particularly preferred ranges are 1 to 6 weight percent of candelilla wax, 1–17 weight percent of beeswax, 3–8 weight percent of stearic acid, 1–5 weight percent of glyceryl monostearate. Other waxes might be used as well, such as carnauba wax, wool wax, hardened paraffin, ceresine wax, ozokerite, silicon and mixtures thereof.

The share of polyethylene is 2 to 10 weight percent relative to the share of the oil phase.

A particularly preferable polyethylene is Perfomalene 400® (New Phase Technology, Piscataway, N.J., USA) which does not contain any branches and therefore is a very flexible polyethylene.

Another preferred feature of the present invention is that the oil phase has a total penetration value of 5–20 dyn/mm at 25° C. This means that the mixture of polyethylene, other waxes, esters, emulsifying agents, etc. existing in most cases in the oil phase has a penetration value within the aforementioned range.

Emulsifying agents to be used are for example sorbitan fatty acid ester, esters of $C_{12}$–$C_{22}$ fatty acids and glycerin, polyglycerin, pentaerythrite, sugar alcohols (e.g. sorbite), polyglucosides (e.g. cellulose); polyalkylene glycols; wool wax alcohols. Preferably, 0.2 to 2 weight percent of sorbitan oleate are used.

The external film-forming agents polyurethane-1 or PEG/PPG-25/25 dimethicone/acrylates copoloymer (Luviflex Silk®) or a mixture of both substances are normally used almost exclusively in hairsprays only. In the present case, the terpolymer film-forming agent comprising t-butylacrylate, methacrylic acid and dimethicone copolyol is present in a preferred share of 0.5 to 10 weight percent relative to the total weight of the mascara compound.

Preferably, the aqueous phase of the mascara according to the present invention comprises a film-forming agent too, which is particularly selected among PVP/PVP-VA, vinyl caprolactame/vinyl pyrrolidon/quaternized vinylimidazol (Polyquaternium-46) and mixtures thereof. The aqueous phase may further contain thickeners, hydroxy ethyl cellulose, neutralization agents, and triethanolamine.

Further, the stretch mascara comprises organic and inorganic pigments, pigment mixtures or powders having a pigment-like effect including powders having a pearl-gloss effect. These may comprise, for example, iron oxides, natural aluminum silicates such as ochre, titanium dioxide, mica, kaolin, manganese-containing clays such as umbra and red bolus, calcium carbonate, talc, mica/titanium oxide, mica/ titanium oxide/iron oxide and mixtures thereof. The percentage share of the dying pigments or mixtures thereof may range from 7 to 15 weight percent.

Other preferred components of the stretch mascara according to the present invention are hair conditioning agents such as vitamin E or vitamin E-acetate ranging from 0.1 to 2 weight percent and/or panthenol ranging from 0.1 to 1.2 weight percent. As a particularly preferred additive the mascara may comprise 0.1 to 4 weight percent of an aqueous extract of the rhodophycea alga providing for an improved effectiveness with regard to the stability of hair and the improvement of a natural appearance.

Anti-oxidants such as vitamin C and derivatives thereof, such as ascorbyl acetate, ascorbyl phosphate and ascorbyl palmitate; vitamin A and derivatives thereof; folic acid and derivatives thereof; vitamin E and derivatives thereof such as tocopheryl acetate; flavones or flavonoids; amino acids such as histidine, glycine, tyrosine, tryptophane and derivatives thereof; carotinoids and carotines may be contained therein as well.

The addition of UV filters soluble in water or oil, i.e. UVA or UVB filters or both, is advantageous. Preferred UVB filters soluble in oil include 4-aminobenzoic acid derivates such as 4-(dimethylamino) benzoic acid (2-ethylhexyl) ester; esters of cinnamic acid such as 4-methoxy cinnamic acid (2-ethylhexyl) ester, benzophenone derivates such as 2-hydroxy 4-methoxyben-zophenone; 3-benzylidene camphor derivates such as 3-benzylidene camphor. Preferred UV filters soluble in oil are benzophenone-3, butyl methoxybenzoyl methane, octyl methoxycinnamate, octyl salicylate, 4-methyl benzylidene camphor, homosalate and octyl dimethyl PABA.

It is preferably to add humectants such as Propylene Glycol, Butylene Glycol, Glycerin or mixtures thereof.

The addition of emollients such as Panthenol is preferred, e.g. in a concentration of 0.1-1 weight %. Also other emollients are useful such as stearates or palmitates.

Generally and in contrast to common mascara compounds offered in the market, the specific polyethylene and the combination of internal and external film-forming agents bring about a considerable "stretching" effect after applying the compound. This stretching effect on the eyelashes results in a significantly prolonged durability and an excellent contact with the underlying hair. Further, curling of the eyelashes is facilitated so that the eyelashes appear to be longer and more voluminous. The compound can be applied in a smudge-proof and flake-proof manner and remains in this state. No sticking of the eyelashes occurs, and pigments can be distributed very well in the emulsion and thus on the eyelashes too.

The mascara can be removed easily by using water and soap.

Another advantageous feature of the stretch mascara according to the present invention is that its viscosity ranges from 50,000 to 500,000 Pa·s (cP) measured according to the Brookfield method using spindles TC/TD/TE at 25° C. and in the range of 50–75% of the spindle speed. A preferred viscosity range is 140.000 to 350.000 Pa·s.

Due to this low viscosity compared with prior art products having a viscosity of approx. 1,500,000 Pa·s (cP), the mascara is of creamy consistency, can be stored in this consistency considerably longer than conventional products and further has a significantly longer consumption life after being opened the package and used by the consumer.

The invention further relates to a method for manufacturing a stretch mascara, which comprises that after mixing the oil and water phases an external film-forming phase is added where PEG/PPG-25/25 Dimethicone/Acrylates/t-Butyl Acrylates Copolymer is added in small portions at 40–76° C., preferred 70–76° C. Only by that processing it is possible to avoid a strong viscosity increasing and a gum-like character of the mixture.

Now, the present invention will be further explained by examples. Unless specified otherwise, all data are given as weight percent.

| Examples 1–4: Mascara 1–VI | 1 | 2 | 3 | 4 |
|---|---|---|---|---|
| Polyethylene | 1.2 | 0.5 | 2 | 3 |
| Candelilla wax (Euphorbia cerifera) | 2.4 | 3 | 1 | 4 |
| Stearic acid | 5.5 | 4.6 | 4 | 5 |
| Glyceryl monostearate | 3.5 | 3 | 3 | 3.3 |
| Beeswax | 2.7 | 3 | 2 | 4 |
| Sorbitan Sesquioleate | 0.6 | 0.6 | 0.4 | 0.4 |
| Polybutene | 0.3 | 0.1 | 0.5 | — |
| Propylparaben | 0.2 | 0.2 | 0.2 | 0.3 |
| Hydroxyethyl cellulose | 0.3 | 0.5 | 0.2 | 0.5 |
| PVP (Polyquaterniuin-46) | 2.5 | 2.7 | 3 | 3.1 |
| Triethanolamine | 1.1 | 1.5 | 0.8 | 1 |
| Black Iron Oxide | 12 | 13 | 11 | 5 |
| Water | ad 100 | ad 100 | ad 100 | ad 100 |
| Cellulose | 1 | 0 | 2 | — |
| Polyurethane-1 | 8 | 9 | 13 | 15 |
| PEG/PPG-25/25 Dimeticone/acrylates/t-butyl acrylates (Luviflex"Silk) | 1.2 | 2 | 1 | 1.8 |
| Methylparaben | 0.2 | 0.2 | 0.2 | 0.4 |
| Tocopheryl Acetate | 0.2 | 0.5 | 1 | 0.5 |
| Panthenol 50% AQ. | 0.2 | 1 | 0.7 | 0.6 |
| Bioextender/Water hydrolyzed Rhodyphycea extract | 0.4 | 0.8 | 1.7 | — |
| Phenonip (Paraben mixture) | 0.3 | 0.2 | 0.3 | 0.3 |

The polyethylene used has the following parameters in examples 1, 2 and 3: Molecular weight 500, melting point 88° C., penetration value 7. In example 4: MW 400, Mp. 79.5° C., penetration value 15.

At first all waxes, stearic acid, polyethylene, polybutylene, sorbitan sesquioleate and propylparaben are heated to about 95° C. and stirred to receive a clear liquid. Separately water is heated and the cellulose is added. The temperature of the watery phase is raised to about 65° C. and PVP, black iron oxide and methyl paraben is added during mixing. At 85° C. the oily phase is added to the watery phase during mixing for receiving an emulsion. After that Luviflex Silk® is added at 74–76° C. and in small portions under stirring to avoid a gum-type mixture. Further after addition of Polyurethane-1 at about 65° C. and further decreasing the temperature to about 45° C. the remaining components are added. The mixture is homogenized to receive a creamy consistence of the final product.

The invention claimed is:

1. A stretch mascara containing an oil phase and an aqueous phase, which comprises
   a) the oil phase comprises 2 to 10% by weight, based on the total weight of the oil phase, of an unbranched polyethylene having a molecular weight distribution ranging between 400 and 1,500 Dalton, and further comprising at least one oil or wax or mixture thereof;
   b) the aqueous phase comprises 0.5 to 5% by weight, based on the total weight of the mascara, of a film-forming agent for the aqueous phase selected from the group consisting of PVP/PVP-VA, vinylcaprolactam/vinylpyrrolidone/quaternized vinylimidazole and mixtures thereof;

c) additionally 0.5 to 20% by weight, based on the total weight of the mascara, of an external phase of a film-forming agent comprising a water soluble film-forming agent selected from the group consisting of PEG/PPG-25/25 dimethicone/acrylates/t-butyl acrylates copolymer, polyurethane-1 and mixtures thereof; and d) further cosmetic pigments, carriers and auxiliary substances to make 100% by weight.

2. The stretch mascara according to claim 1, wherein the oil phase has a needle penetration value in the range of 5–20 dyn/mm at 25° C.

3. The stretch mascara according to claim 1, wherein the unbranched polyethylene has a molecular weight distribution ranging between 400 and 600 Dalton.

4. The stretch mascara according to claim 1, wherein the oil phase further comprises natural waxes, synthetic waxes, emollients, higher $C_{12}$–$C_{20}$ fatty acid esters, emulsifying agents, protective agents and mixtures thereof.

5. The stretch mascara according to claim 4, wherein the waxes are selected among candelilla wax, beeswax, stearic acid, glyceryl monostearate and mixtures thereof.

6. The stretch mascara according to claim 1, wherein the the oil phase is 10 to 40 weight percent relative to the total weight of the mascara.

7. The stretch mascara according to claim 1, wherein the PEG/PPG-25/25 dimethicone/acrylates/t-butyl acrylates copolymer is 0.5 to 10 weight percent relative to the total weight of the mascara.

8. The stretch mascara according to claim 1, wherein the aqueous phase comprises an aqueous extract of the rhodophycea algae.

9. The stretch mascara according to claim 1, wherein said stretch mascara has a viscosity ranging from 50,000 to 500.000 Pa·s, measured according to the Brookfield method using spindles TC/TD/TE at 25° C.

10. A method for manufacturing a stretch mascara, which comprises (a) mixing an oil phase and an a an aqueous phase,
wherein said oil phase comprises 2 to 10% by weight, based on the total weight of the oil phase, of an unbranched polyethylene having a molecular weight distribution ranging between 400 and 1,500 Dalton, and further comprising at least one oil or wax or mixture thereof;
wherein the aqueous phase comprises 0.5 to 5% by weight, based on the total weight of the mascara, of a film-forming agent for the aqueous phase selected from the group consisting of PVP/PVP-VA, Vinylcaprolactam/Vinylpyrrolidone/quaternized Vinylimidazole and mixtures thereof;

(b) after step (a), adding an external film-forming phase, comprising adding PEG/PPG-25/25 dimethicone/acrylates/t-butyl acrylates copolymer in small portions at 40–76° C.

* * * * *